United States Patent [19]

Berg

[11] Patent Number: 5,052,924

[45] Date of Patent: Oct. 1, 1991

[54] FIBEROPTIC IMAGING DENTAL DRILL

[76] Inventor: Randy J. Berg, 6813 W. 83rd St. Terr., Bloomington, Minn. 55438

[21] Appl. No.: 612,596

[22] Filed: Nov. 13, 1990

Related U.S. Application Data

[63] Continuation-in-part of Ser. No. 316,927, Mar. 22, 1989.

[51] Int. Cl.$^5$ ............................................... A61C 1/00
[52] U.S. Cl. ....................................... 433/29; 433/114
[58] Field of Search .................. 433/29, 30, 31, 141, 433/114, 229; 128/4, 6

[56] References Cited

U.S. PATENT DOCUMENTS

| | | | |
|---|---|---|---|
| 4,184,175 | 1/1980 | Mullane, Jr. | 433/29 |
| 4,403,956 | 9/1983 | Nakanishi | 433/82 |
| 4,727,416 | 2/1988 | Cooper et al. | 433/29 |
| 4,858,001 | 8/1989 | Milbank et al. | 433/29 |
| 4,917,603 | 4/1990 | Haack | 433/84 |

Primary Examiner—Cary E. Stone

[57] ABSTRACT

A device for enabling visualization of the frontal proximity of the turbine housing of a dental drill, which comprises an air turbine dental drill, a coherent fiberoptic imaging scope, and an electronic means of video registration. By functioning as an integral unit, the device allows the combined control of visualization and drilling capabilities with just one hand.

3 Claims, 1 Drawing Sheet

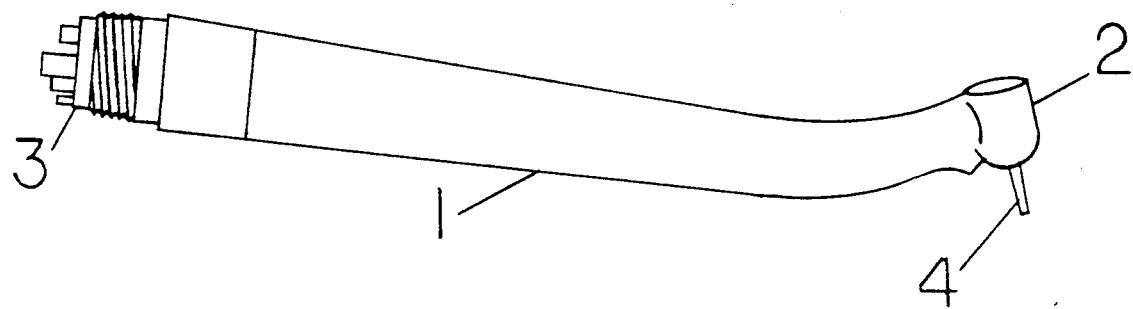
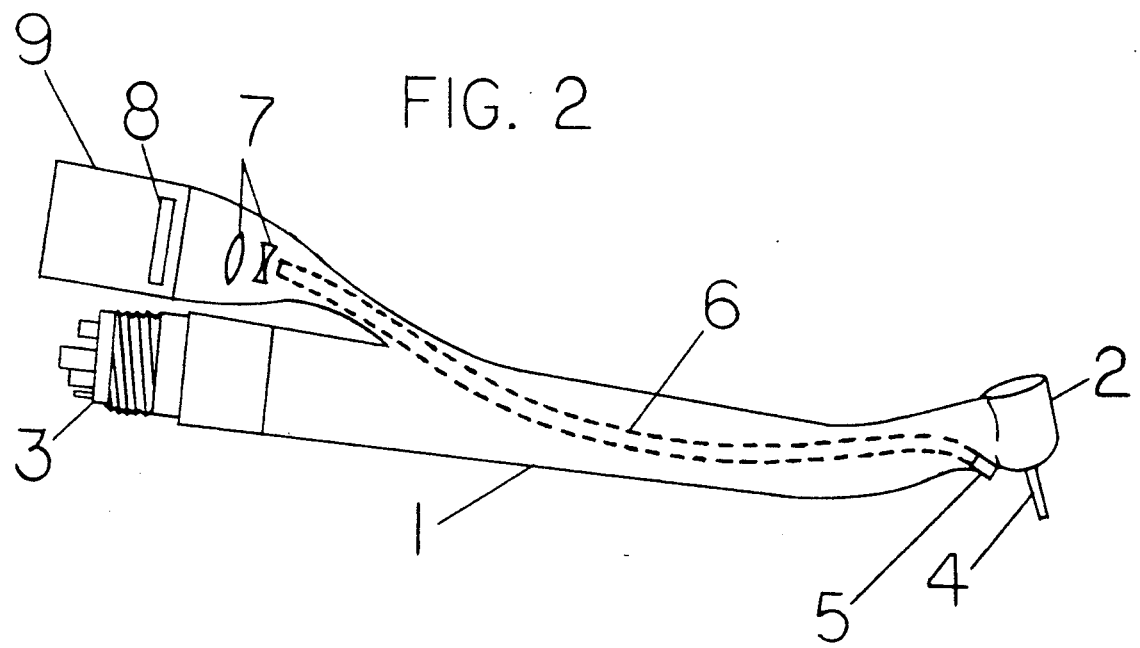

FIBEROPTIC IMAGING DENTAL DRILL

This is a continuation in part patent application for application Ser. No. 07/316,927 filed by Randy Berg on 03/22/89 (pending) for an invention titled Fiberoptic Imaging Dental Drill.

BACKGROUND OF THE INVENTION

1. Field of the Invention

The invention relates to a device for enabling visualization of the frontal proximity of the turbine housing of a dental drill by means of a coherent fiberoptic imaging scope.

2. Description of the Prior Art

Dental drills currently use non-coherent fiberoptic bundles to provide lighting to the frontal proximity of the turbine housing to illuminate their work subject. Visualization of the work is accomplished directly when possible, or by use of a dental mirror.

Use of a dental mirror requires use of another hand, is often hampered by lack of space, and also requires viewing to be done from behind the dental drill, while drilling is being done. This invention eliminates these problems.

SUMMARY OF THE INVENTION

The invention relates to a device which allows visualization of the frontal proximity of the turbine housing of a dental drill. It comprises a coherent fiberoptic imaging scope as a means for conveying an image from the frontal area of the dental drill turbine housing to an electronic means of video registration.

BRIEF DESCRIPTION OF THE DRAWINGS

FIG. 1 is a drawing of a conventional dental drill.
FIG. 2 is a drawing of an embodiment of the Fiberoptic Imaging Dental Drill.

DESCRIPTION OF THE PREFERRED EMBODIMENT

Referring to FIG. 2, an embodiment of the invention is shown in which the Fiberoptic Imaging Dental Drill comprises: I.) an air turbine dental drill, II.) a coherent fiberoptic imaging scope, and III.) an electronic means of video registration.

A commonly available air turbine dental drill comprises: a housing 1 having first and second ends, an air powered turbine within the first end 2, a chuck concentric to the turbine for attaching a dental drill bit 4 at said first end 2 of the housing 1.

Inside the length of the housing 1 there are tubes to deliver: drive air for the turbine, air spray for cooling and debriding the dental drill bit 4, and water spray for cooling and debriding the dental drill bit 4. The tubes for air spray and water spray communicate between the second end 3 of the housing 1 and a point adjacent said attached dental drill bit 4. The drive air tube communicates between the second end 3 of the housing 1 and the air turbine. Exhaust air from the turbine uses the remaining lumen of the housing 1 to communicate with the second end 3 of the housing 1. Dental drills often also have a number of non-coherent fiberoptic bundles which extend from the second end 3 of the housing 1 to a point adjacent said attached dental drill bit 4 to illuminate the work area.

The coherent fiberoptic imaging scope comprises an objective lens and iris system 5 (essentially a miniature camera lens) focused on the adjacent end of the coherent fiberoptic image guide bundle 6, a coherent fiberoptic image guide bundle 6, and an ocular lens system 7.

The electronic means of video registration 8 comprises a solid state video pick up chip such as the CCD or CMOS type chips used as the image pick up portions of most current video cameras.

An image of the dental drill bit 4 and surrounding dental surgical site is focused by the objective lens and iris system 5 onto the adjacent end of the coherent fiberoptic image guide bundle 6. The coherent fiberoptic image guide bundle 6 conveys the image to the opposite bundle end where the ocular lens system 7 in turn focuses the image onto the electronic means of video registration 8. The video pick up chip would be piggy backed to the dental drill and operably connected to additional electronic processing hardware at a remote site.

In the embodiment shown in FIG. 2 the electronic means of video registration is protectively encased in a second housing 9 which detachably couples to the dental drill housing 1. This detachable arrangement allows for easy sterilization of non-electronic parts.

Current surgical scopes often have apparatus to emit fluids across the objective lens of the scope to keep it clear. Air spray and water spray apparatus is previously cited as part of commonly available dental drills and could additionally serve to accomplish lens cleaning in this invention.

The air turbine dental drill, coherent fiberoptic imaging scope, and electronic means of video registration function together to provide a video signal that enables a television monitor to display an image of the dental surgical site. This invention thus combines both visual and surgical capabilities in a single instrument which is controllable with one hand.

I claim:

1. A dental drill comprising:
   a handpiece comprising a housing having first and second ends;
   a dental drill bit located at the first end;
   a coherent fiberoptic imaging scope extending from the first end at a location within the housing adjacent the dental drill bit to a second end located adjacent the second end of the housing; and
   an electronic means of video registration for recording a video image of a work area of a tooth and the dental drill bit, said means operably connected and located adjacent to the second end of the coherent fiberoptic imaging scope.

2. The dental drill of claim 1 wherein the fiberoptic imaging system comprises a coherent fiberoptic bundle and an objective lens and iris system.

3. The dental drill of claim 2 wherein the objective lens and iris system is located at the first end of the coherent fiberoptic system.

* * * * *